United States Patent [19]
Leifeld

[11] Patent Number: 5,642,553
[45] Date of Patent: Jul. 1, 1997

[54] IMAGING APPARATUS FOR SCANNING A CLOTHED ROLL IN A FIBER PROCESSING MACHINE AND METHOD

[75] Inventor: Ferdinand Leifeld, Kempen, Germany

[73] Assignee: Trützschler GmbH & Co. KG, Mönchengladbach, Germany

[21] Appl. No.: 627,067

[22] Filed: Apr. 3, 1996

[30] Foreign Application Priority Data

Apr. 13, 1995 [DE] Germany .................. 195 14 039.7

[51] Int. Cl.[6] .................................................. D01G 15/00
[52] U.S. Cl. .................. 19/98; 19/112; 19/114; 356/237
[58] Field of Search ................ 19/98, 99, 112, 19/114, 0.2, 0.21; 250/562; 356/237, 372; 492/10, 11, 30, 35

[56] References Cited

U.S. PATENT DOCUMENTS

| | | |
|---|---|---|
| 4,272,868 | 6/1981 | Grunder et al. ................ 19/98 |
| 4,953,265 | 9/1990 | Scheinhütte . |
| 5,130,559 | 7/1992 | Leifeld et al. . |
| 5,138,151 | 8/1992 | Inada et al. . |
| 5,355,560 | 10/1994 | Fritzsche et al. ............... 19/98 |

FOREIGN PATENT DOCUMENTS

| | | |
|---|---|---|
| 0 331 039 | 9/1989 | European Pat. Off. . |
| 485881 | 5/1992 | European Pat. Off. ......... 19/98 |
| 0 604 875 | 7/1994 | European Pat. Off. . |
| 37 34 145 | 4/1989 | Germany . |
| 39 28 279 | 2/1991 | Germany . |
| 40 18 847 | 12/1991 | Germany . |
| 677 538 | 5/1991 | Switzerland . |

*Primary Examiner*—Michael A. Neas
*Attorney, Agent, or Firm*—Spencer & Frank

[57] ABSTRACT

A fiber processing apparatus includes a rotary roll carrying a clothing and having an axis and a length measured parallel to roll axis; and an imaging apparatus which has an illuminating device directing a light beam onto a surface area of the clothing, a camera for sensing the light of the surface area lit by the illuminating device and an evaluating device connected to the camera for examining reflected local light intensity changes during rotation of the roll. There is provided an arrangement for presenting to the camera consecutive areas of the clothing surface along the entire roll length and an arrangement for triggering an operation of the camera and/or the illuminating device as a function of the roll rpm.

18 Claims, 6 Drawing Sheets

IMAGING APPARATUS FOR SCANNING A CLOTHED ROLL IN A FIBER PROCESSING MACHINE AND METHOD

CROSS REFERENCE TO RELATED APPLICATION

This application claims the priority of German Application No. 195 14 039.7 filed Apr. 13, 1995.

BACKGROUND OF THE INVENTION

This invention relates to a monitoring apparatus associated with a fiber processing textile machine, such as a carding machine or a roller card unit in which, adjacent to and oriented toward the circumferential surface of a clothed roll or cylinder of the machine, a device for illuminating a surface area of the roll and a camera, such as a light measuring assembly having at least one CCD element are provided. An evaluating device is connected to the camera for evaluating the local light intensity changes of the image generated by the motion of the roll.

In a known apparatus of the above-outlined type, as disclosed, for example, in Published European Application 0 331 039, the fiber layer on the doffer of a carding machine is optically scanned for detecting neps. For this purpose several sensor groups are distributed along the doffer length. Each sensor group scans the fiber layer along an approximately 2.5 cm wide path. The detector groups may move transversely slowly back and forth with an amplitude that corresponds to the path width.

It is a disadvantage of the above-outlined prior art construction that providing a plurality of the sensor groups over the roll length involves a significant constructional outlay. It is a further disadvantage of the conventional arrangement that only a statistical distribution of neps in the fiber layer may be determined since the fiber layer continuously runs at high speeds in the rotary direction of the roll and moves onto the successive roll. The clothing facing the light measuring device is entirely covered by the non-uniformly thick fiber layer; it is only the points of the clothing teeth that may be recognized. The detection of the entire clothing teeth and a detection of the complete roll clothing is not intended by the conventional apparatus and such a complete detection is also not feasible thereby. The purpose of detecting the nep frequency is to draw conclusions concerning machine conditions, for example, the wear of the carding clothing. Thus, conclusions concerning the clothing are drawn indirectly from the number of neps.

SUMMARY OF THE INVENTION

It is an object of the invention to provide an improved apparatus of the above-outlined type from which the discussed disadvantages are eliminated and which, in particular, makes possible a detection and monitoring of the entire clothing teeth and the entire clothing of a clothed roll, such as the main cylinder of a carding machine.

This object and others to become apparent as the specification progresses, are accomplished by the invention, according to which, briefly stated, the fiber processing apparatus includes a rotary roll carrying a clothing and having an axis and a length measured parallel to roll axis; and an imaging apparatus which has an illuminating device directing a light beam onto a surface area of the clothing, a camera for sensing the light of the surface area lit by the illuminating device and an evaluating device connected to the camera for examining reflected local light intensity changes during rotation of the roll. There is provided an arrangement for presenting to the camera consecutive areas of the clothing surface along the entire roll length and an arrangement for triggering an operation of the camera and/or the illuminating device as a function of the roll rpm.

According to an aspect of the invention the clothing surface is scanned by the camera without the presence of fiber material over the entire width of the roll and the image-forming speed and the roll rpm are coordinated with one another. By virtue of this arrangement the clothing teeth on the one hand and the clothing surface of the roll on the other hand can be detected in their entirety. An inspection of the roll surface and the measuring of the teeth of the roll clothing during operation are thus made advantageously possible. Especially the triggering of the camera as a function of the roll rpm is of importance which permits the successive presentation of surface sections of the clothing. A further advantage of the invention resides in the optical measuring of the clothing during operation and the optical measuring of the point distance between the clothing of the flats and the clothing of the carding cylinder.

DESCRIPTION OF THE PREFERRED EMBODIMENTS

Figure 1:
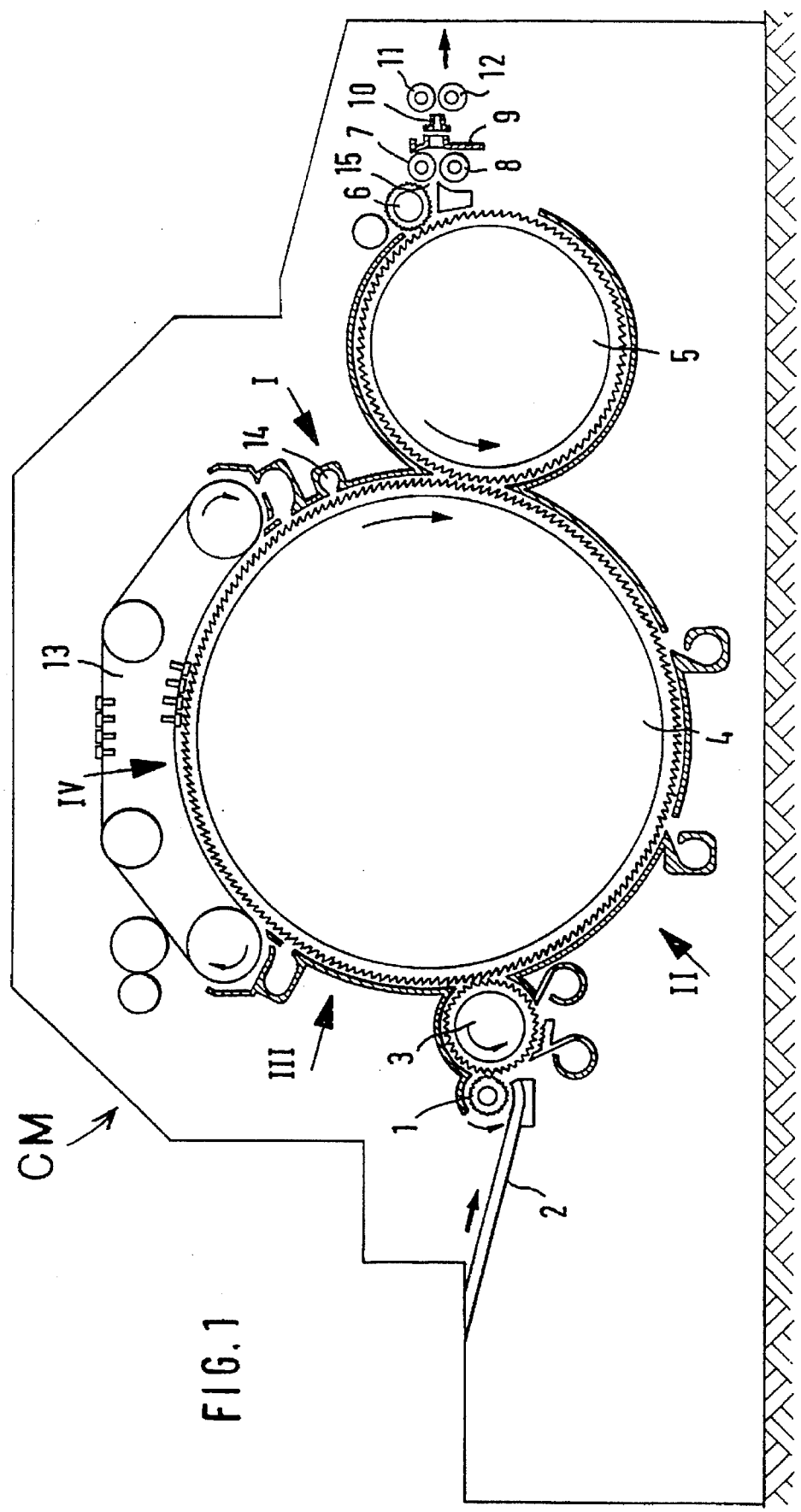
FIG. 1 is a schematic side elevational view of a carding machine incorporating the invention.

FIG. 1 illustrates a carding machine CM which may be, for example, an EXACTACARD DK 760 model manufactured by Trützschler GmbH & Co. KG, Mönchengladbach, Germany. The carding machine CM includes a feed roll 1, a feed table 2 cooperating with the feed roll 1, a licker-in 3, a main carding cylinder 4 (having an rpm of 260–600 and a diameter of 1290 mm), a doffer 5, a stripper roll 6, cooperating crushing rolls 7, 8, a web guiding element 9, a sliver-forming trumpet 10, cooperating calender rolls 11 and 12 as well as travelling flats 13. The rotation of the various rolls of the carding machine is indicated by respective curved arrows. Arrows I–IV designate regions of the carding machine CM where an apparatus according to the invention may be associated with the carding cylinder 4.

Figure 2:
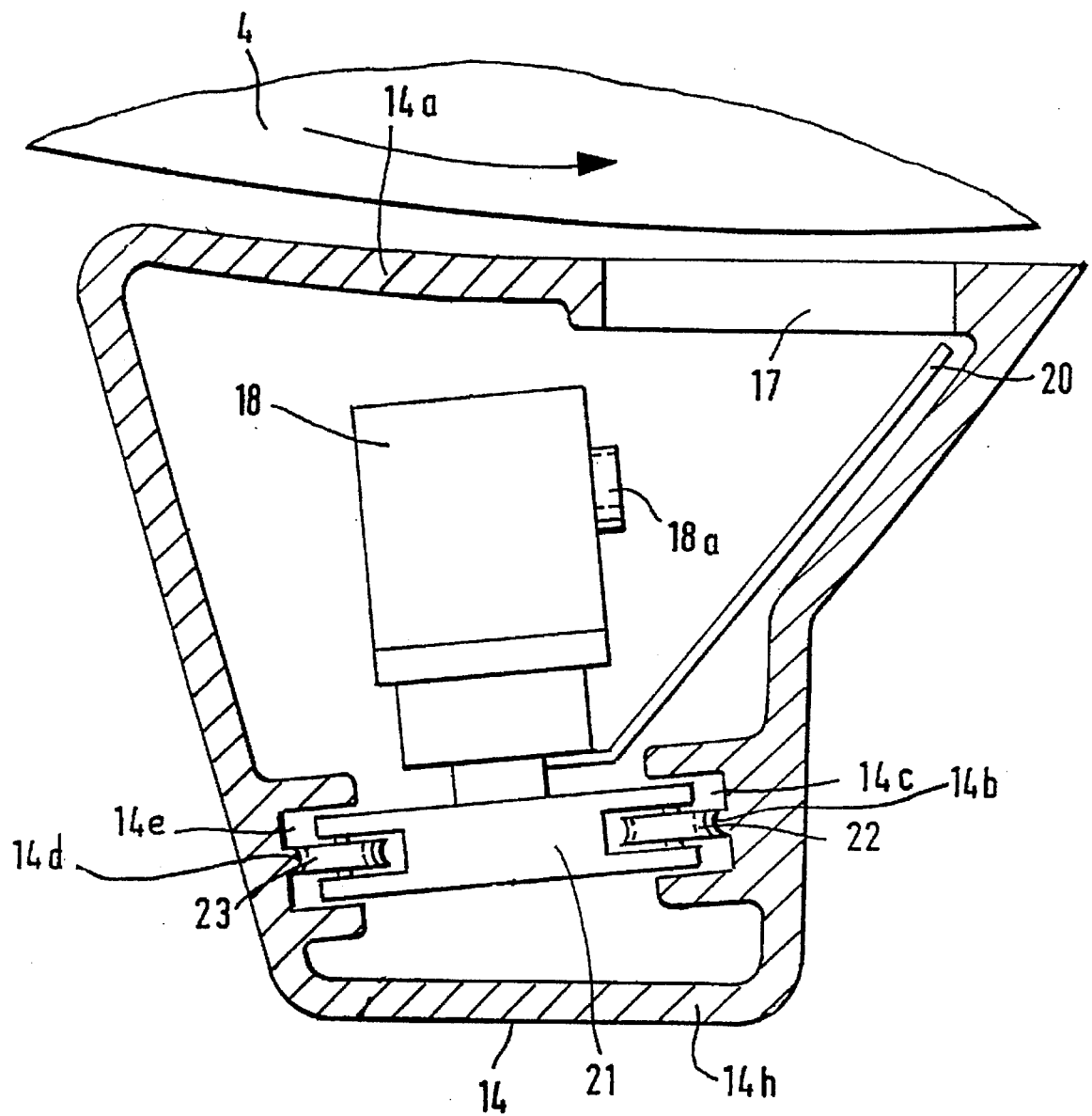
FIG. 2 is a sectional side elevational view of a preferred embodiment of the invention, illustrating a camera mounted on a camera carriage displaceable within a housing.
Figure 3:
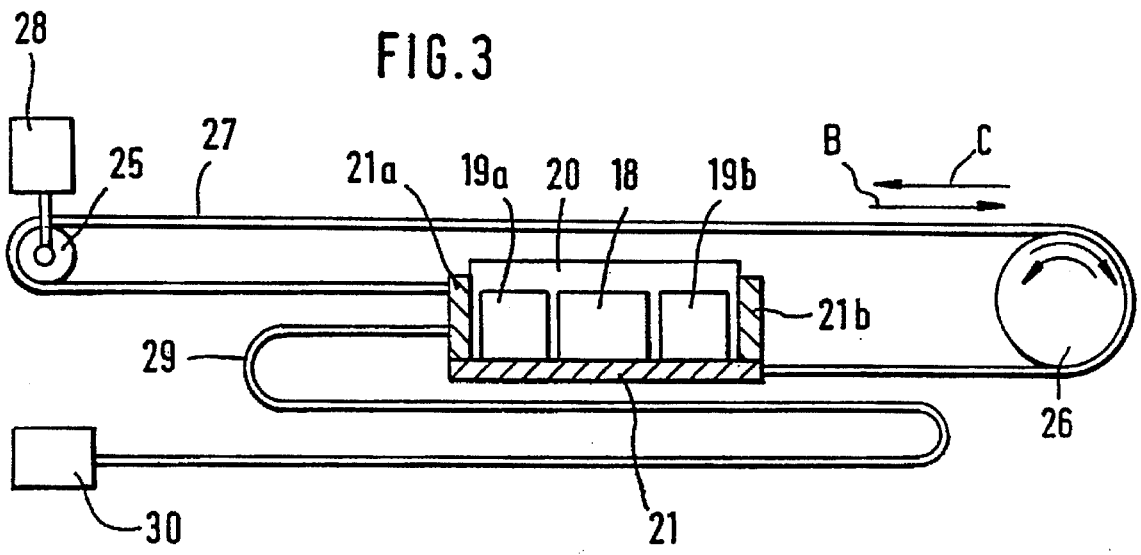
FIG. 3 is a schematic side elevational view illustrating a cable drive for the camera carriage.
Figure 4:
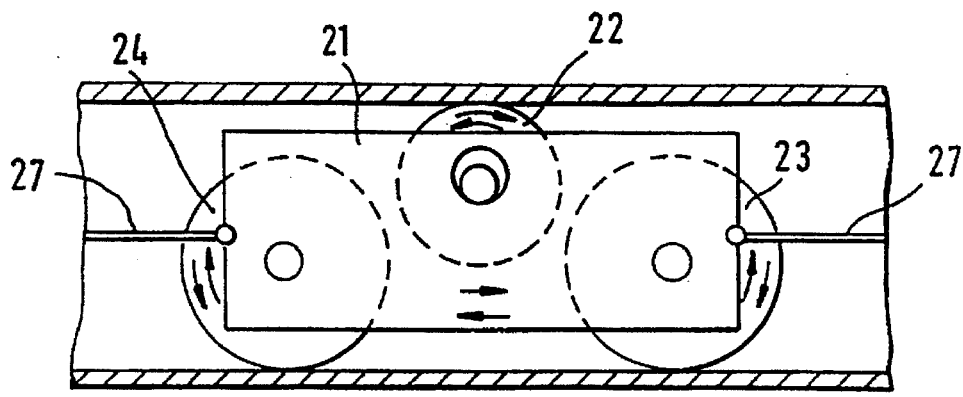
FIG. 4 is a schematic fragmentary top plan view of the camera carriage and guide wheels therefor.

Also referring to FIGS. 2, 3 and 4, a housing 14 is provided which may be an extruded aluminum component and which may be positioned, for example, in region I of the carding cylinder 4. The housing 14 extends substantially along the entire axial length of the cylinder 4 and has a longitudinally extending, light-transparent window 17 in the housing wall 14a oriented towards the clothing of the cylinder 4.

The housing 14 accommodates a camera 18 and illuminating devices 19. The camera 18 may be a diode-line camera, while the illuminating devices 19 may include a plurality of light diodes, strobo-lights, or the like. The camera 18 and the illuminating devices 19 are mounted on a carriage 21, together with a mirror 20 arranged in such an angle as to establish a line of sight between an objective lens 18a of the camera 18 and the illuminating devices 19, on the one hand and the clothing of the cylinder 4, on the other hand.

The carriage 21 has three guide wheels 22, 23 and 24. The guide wheel 22 runs on a rail 14b extending in a trough 14c longitudinally of the housing 14, while the guide wheels 23 and 24 which are arranged on a side of the carriage 21 opposite the guide wheel 22, run on a rail 14d extending in a trough 14e longitudinally of the housing 14.

With particular reference to FIG. 3, the two ends of a pull cable 27 are attached to respective opposite end faces 21a, 21b of the carriage 21. At opposite ends of the housing 14 the cable 27 is supported by end rollers 25 and 26. A motor 28 drives the roller 25 to thus displace the carriage 21 in the direction B or C. Electric conductors, preferably combined into a flexible flat cable 29, connect the camera 18 and the illuminating devices 19 with an electronic control and regulating device such as a microcomputer 30.

Figure 5:
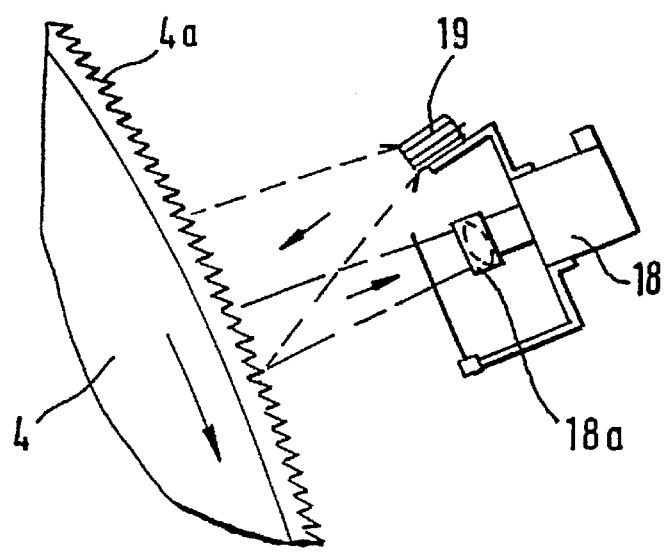
FIG. 5 is schematic side elevational view of another preferred embodiment of the invention.

According to the arrangement shown in FIG. 5, a single illuminating device is provided which is directed towards the clothing 4a of the carding cylinder 4 at an incident angle of less than 90°. The light reflected from the illuminated surface area of the clothing 4a of the carding cylinder 4 directly enters the objective 18a of the camera 18.

Figure 6:
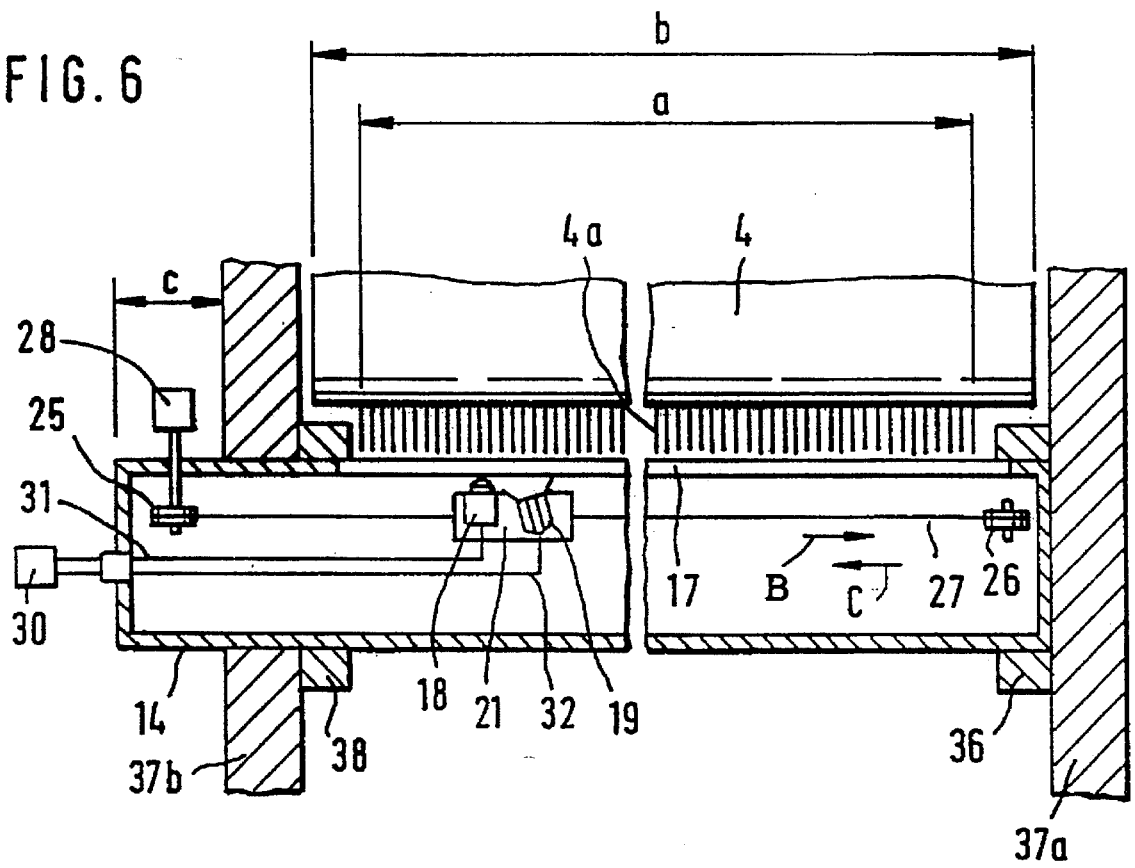
FIG. 6 is a schematic sectional front elevational view of yet another preferred embodiment of the invention.

In the embodiment illustrated in FIG. 6, one end of the housing 14 may be inserted into a socket 36 which is affixed to the carding frame 37a and whose receiving space is complemental with the peripheral outline of the housing 14 to provide for a form-fitting engagement between the components 14 and 36. When in the installed position as illustrated in FIG. 6, the outer end face of the housing 14 is in a face-to-face engagement with the inner surface of the frame 37a. The other end region of the housing 14 passes through aligned apertures provided in a guide bracket 38 and the frame portion 37b of the carding machine. At this end too, the housing 14 is form-fittingly supported and is thus firmly positioned in the carding frame during operation. The housing 14 may further be secured by screws (not shown) against displacement. One end of the housing 14 projects beyond the frame 37b by a distance c, whereby a grip is provided for facilitating replacement. The two cable pulleys 25 and 26, supporting the cable 27 are positioned inside the housing 14. The camera 18 and the illuminating device 19 mounted on the carriage 21 are oriented toward the clothing 4a and thus a light-deflecting mirror as described in connection with FIG. 2 is not needed. The camera 18 and the illuminating device 19 are connected with respective conductors 31 and 32 to the control and regulating device 30. The axial length of the carding cylinder 4 is designated at b whereas the axial length of the clothing 4a is designated a.

Figure 7A:
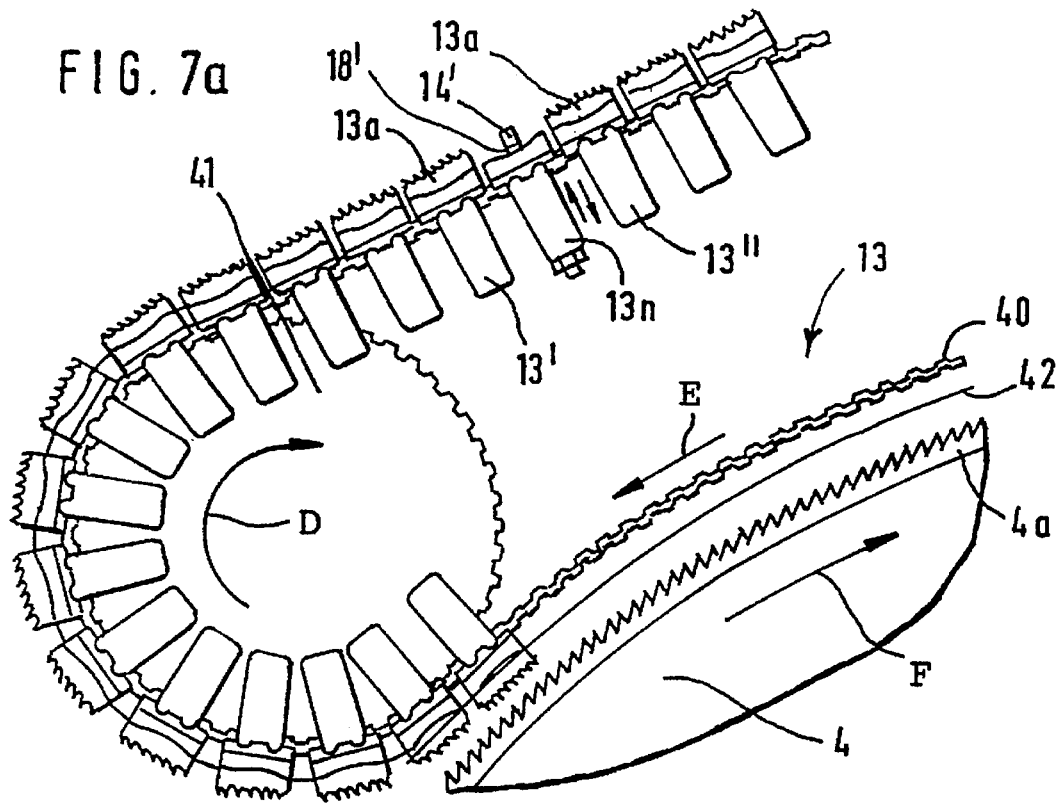
FIGS. 7a and 7b are schematic side elevational views of one end of travelling flats illustrating yet another embodiment of the invention.
Figure 7B:
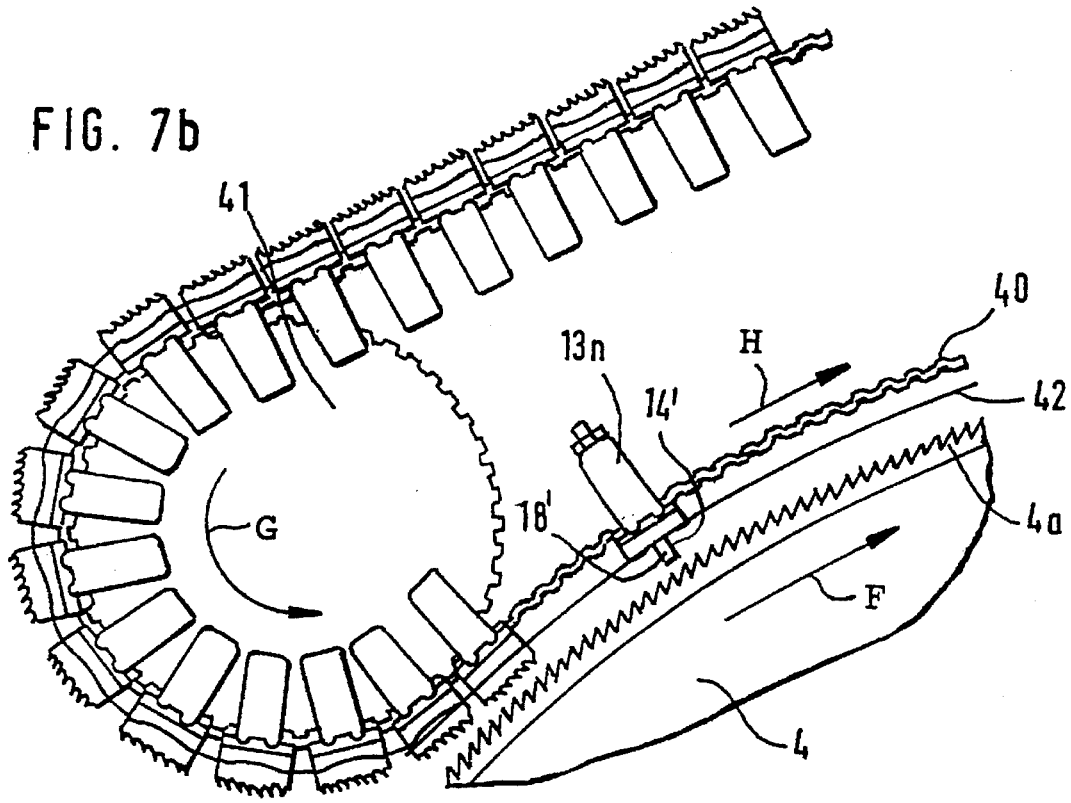

According to an embodiment illustrated in FIGS. 7a and 7b, a housing 14', accommodating a camera 18' and a nonillustrated illuminating device, is inserted into a flat bar 13n of the travelling flats 13 of the card. To ensure proper operation of the monitoring apparatus, the flat bar 13n is without the usual clothing. The housing 14', with all the equipment inside, may be replaced, by a normal (clothed) flat bar 13' either during standstill or during machine run. The FIGS. 7a and 7b show the arrangement of the flat bar 13n between the flat bars 13' and 13" which, similarly to all the other flat bars, are provided with a flat clothing 13a. A fine thread arranged at the rear terminus of the housing 14' provides for an exact setting of the position of the camera 18' relative to the cylinder clothing 4a and/or the flat clothing 13a. In FIG. 7a, similarly to the arrangement of FIG. 1, the frontal end roller 41 supporting the toothed belt 40 (which moves the flat bars that glide on the sliding guide 42) rotates in a clockwise direction D, thus moving the flat bars in a direction E, opposite to direction F in which the clothing 4a travels in the region adjoining the flat bars. In contrast, in the FIG. 7b arrangement the end roller 41 rotates counterclockwise in the direction G, causing the flat bars to co-travel with the clothing 4a in the direction H.

Figure 8:
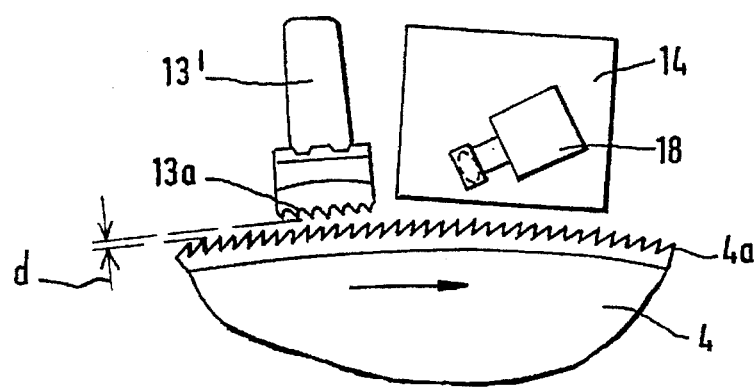
FIG. 8 is a schematic side elevational view of a relative positioning of a camera with respect to a carding cylinder and a travelling flat bar.

Referring now to FIG. 8, in the embodiment shown therein the housing 14" takes the place of two consecutive flat bars. The camera 18" is oriented at an angle of incidence that is less than 90° with respect to the clothing 4a of the carding cylinder 4. In this manner, the gap d between the flat bar 13' and the clothing 4a of the carding cylinder 4 may be observed. This embodiment may also be used during processing of fiber material, so that the behavior of the fiber material during the carding process may be monitored and evaluated.

Figure 9:
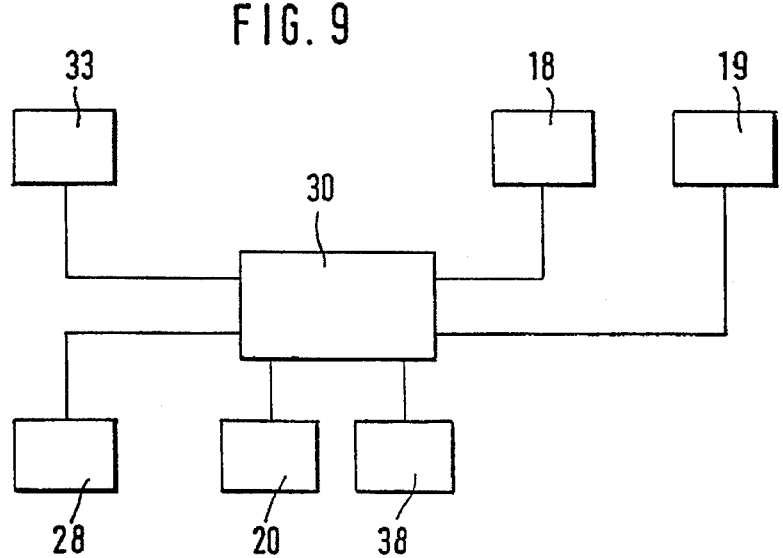
FIG. 9 is a block diagram illustrating an electronic control and regulating device for operating the camera, the illuminating device, the image evaluating device and a triggering device according to the invention.

FIG. 9 shows the electronic control and regulating device 30 to which the camera 18, the illuminating device 19, an image processing device 20, the drive (such as the electric motor 28) for the carriage 21, an rpm-measuring device 33 sensing the rpm of the cylinder 4 and a triggering device 38 are attached. The triggering device 38 emits a triggering or initiating signal for pulse generators or for the deflection timing of a cathode ray oscilloscope. The triggering signal consists either of an externally applied pulse or is derived from the measuring signal of the oscilloscope. The circuit for such an arrangement is formed essentially of a comparator which unlocks a sawtooth generator as soon as the measuring voltage has exceeded a settable threshold magnitude. In this manner it is ensured that on a viewing screen still images are obtained because a synchronization with the frequency of the signal to be displayed occurs.

Figure 10:
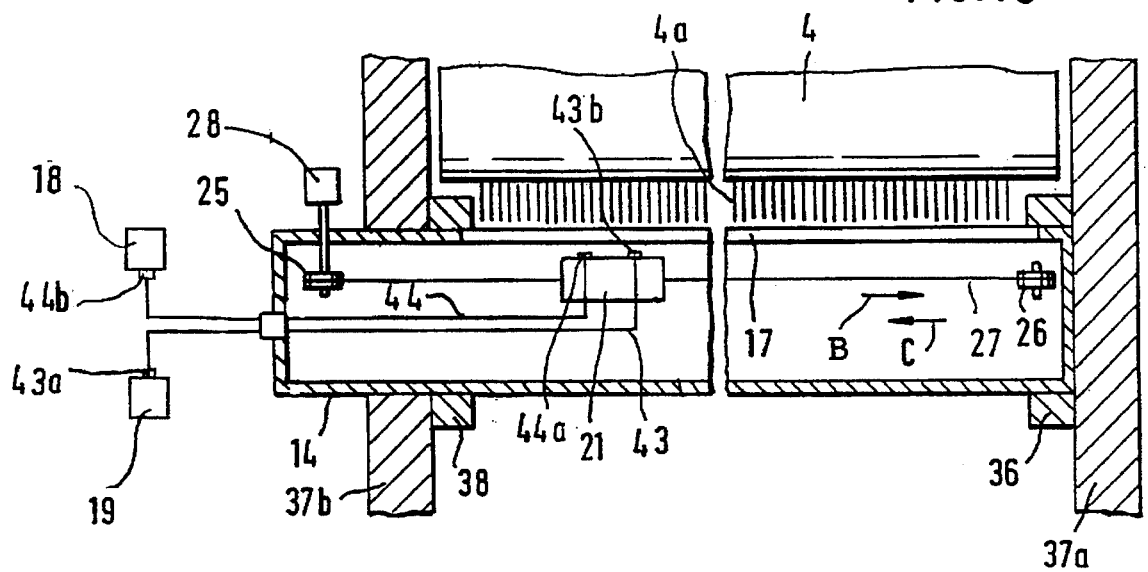
FIG. 10 is a schematic sectional front elevational view of yet another preferred embodiment of the invention.

It will be understood that the invention may be practiced by using a camera and an illuminating device which are held stationarily remote from the clothing surface to be examined. In such an arrangement, as illustrated in FIG. 10, an optical fiber cable (optical wave guide) 43 is provided which has an input end 43a connected to the illuminating device 19 and an output end 43b mounted on a carriage 21' and oriented toward the clothed roll (such as the carding cylinder 4) for directing light onto the roll clothing. Further, an optical fiber cable 44 is provided, whose input end 44a is mounted on the carriage 21' to receive light reflected from the roll clothing and an output end 44b connected to the camera 18. This solution is particularly advantageous when only very limited space is available.

It will be understood that the above description of the present invention is susceptible to various modifications, changes and adaptations, and the same are intended to be comprehended within the meaning and range of equivalents of the appended claims.

What is claimed is:

1. In a fiber processing apparatus including a rotary roll carrying a clothing and having an axis and a length measured parallel to said axis; and an imaging apparatus including an illuminating device directing a light beam onto a surface area of said clothing;

a camera for sensing the light of the surface area lit by said illuminating device; and an evaluating device connected to said camera for examining reflected local light intensity changes during rotation of said roll;

the improvement comprising (a) means for presenting to the camera consecutive areas of the clothing surface along the entire roll length; and (b) means for triggering an operation of at least one of said camera and said illuminating device as a function of an rpm of said roll.

2. The fiber processing apparatus as defined in claim 1, wherein said means for presenting comprises (a) an optical wave guide having a first input connected to said illuminating device, a first output for emitting light from said illuminating device onto said clothing, a second input for receiving reflected light from said clothing and a second output connected to said camera; and (b) displacing means for moving said first output and said second input of said optical wave guide parallel to said axis.

3. The fiber processing apparatus as defined in claim 1, wherein said illuminating device is positioned adjacent said clothing and directs a light beam onto a surface area of said clothing; further wherein said camera is positioned adjacent said clothing; and said means for presenting comprising displacing means for moving said camera parallel to said axis.

4. The fiber processing apparatus as defined in claim 3, further comprising a housing accommodating said camera and said illuminating device; said housing having a length extending parallel to the roll length and a light-transparent window extending along the housing length; further comprising supporting means for positioning said housing adjacent said roll during operation.

5. The fiber processing apparatus as defined in claim 4, wherein said means for presenting comprises a carriage supporting said camera and said illuminating device and guide means for guiding said carriage for motion along the housing length.

6. The fiber processing apparatus as defined in claim 5, wherein said guide means comprises runner wheels mounted on said carriage and rails held within said housing and extending parallel to said housing length; said wheels running on said rails.

7. The fiber processing apparatus as defined in claim 5, further comprising a mirror mounted on said carriage and being oriented such as to provide a line of sight through said window between the illuminating device and the clothing and between the clothing and the camera.

8. The fiber processing apparatus as defined in claim 5, wherein said camera and said illuminating device are oriented such as to be in a direct line of sight with said clothing.

9. The fiber processing apparatus as defined in claim 5, wherein said means for presenting further comprises two end rollers supported in said housing at opposite ends thereof; a pull cable attached to said carriage and a motor driving one of said end rollers for displacing said carriage by said pull cable.

10. The fiber processing apparatus as defined in claim 5, wherein said fiber processing machine includes a machine frame and further wherein said housing is stationarily supported in said machine frame.

11. The fiber processing apparatus as defined in claim 10, wherein said machine frame comprises first and second frame members situated adjacent opposite longitudinal ends of said roll; further comprising a socket affixed to said first frame member and receiving an end of said housing and an aperture provided in said second frame member; said housing passing through said aperture.

12. The fiber processing apparatus as defined in claim 11, wherein said aperture is in alignment with said socket, whereby said housing is introducible through said aperture and, by sliding therethrough, receivable in said socket.

13. The fiber processing apparatus as defined in claim 11, wherein said socket and said aperture are complemental to a peripheral outline of said housing, whereby said housing is form-fittingly received in said socket and in said aperture.

14. The fiber processing apparatus as defined in claim 4, wherein said fiber processing machine is a carding machine having a main carding cylinder constituting said clothed roll and a travelling flats assembly; said travelling flats assembly having flat bars for cooperating with said carding cylinder and means for moving the flat bars along a peripheral portion of said carding cylinder; said housing being carried by one of said flat bars.

15. The fiber processing apparatus as defined in claim 14, wherein upon travel along said peripheral portion, said camera is oriented at an oblique angle of incidence to said clothing for monitoring a gap formed between the roll clothing and a clothing of one of said flat bars.

16. The fiber processing apparatus as defined in claim 1, wherein said camera is a diode-line camera.

17. The fiber processing apparatus as defined in claim 1, wherein said means for presenting includes a drive motor and said means for triggering includes an rpm sensor for sensing an rpm of said roll and a triggering device; further comprising an electronic control and regulating device; said drive motor, said rpm sensor, said illuminating device, said camera, said evaluating device and said triggering device being connected to said electronic control and regulating device.

18. A method of examining the clothing of a clothed roll in a textile fiber processing machine, comprising the following steps:

(a) operating said machine in an empty run whereby said roll rotates in the absence of fiber material thereon;

(b) illuminating subsequent surface portions of said clothing along substantially the entire axial length of said roll by means of an illuminating device moved parallel to the roll length;

(c) simultaneously with the illuminating step, sensing the light of the surface area lit by step (b);

(d) applying signals from said camera to an evaluating device connected to said camera for examining reflected local light intensity changes during rotation of said roll; and (e) triggering the operation of at least one of said camera and said illuminating device as a function of an rpm of said roll.

* * * * *